United States Patent [19]

Axen

[11] 4,212,986
[45] Jul. 15, 1980

[54] 2,2-DIFLUORO-PGE$_2$ ANALOGS

[75] Inventor: Udo F. Axen, Plainwell, Mich.

[73] Assignee: The Upjohn Company, Kalamazoo, Mich.

[21] Appl. No.: 724,109

[22] Filed: Sep. 17, 1976

Related U.S. Application Data

[62] Division of Ser. No. 552,708, Feb. 24, 1975, Pat. No. 4,001,300.

[51] Int. Cl.$^2$ .............................................. C07C 177/00
[52] U.S. Cl. ................................... 560/121; 562/503; 260/408
[58] Field of Search .............. 260/468 D, 514 D, 408; 560/121; 562/503

[56] References Cited

U.S. PATENT DOCUMENTS

| | | | |
|---|---|---|---|
| 3,816,393 | 6/1974 | Hayashi | 260/468 |
| 3,847,967 | 12/1974 | Lincoln et al. | 260/468 |
| 3,892,795 | 1/1975 | Magerlin | 260/468 |
| 3,919,286 | 11/1975 | Bundy et al. | 260/468 |
| 3,962,293 | 6/1976 | Magerlin | 260/468 |
| 3,981,880 | 9/1976 | Schneider | 260/468 |

*Primary Examiner*—Robert Gerstl
*Attorney, Agent, or Firm*—Robert A. Armitage

[57] ABSTRACT

2,2-Difluoro prostaglandin E, F$_\alpha$, F$_\beta$, A, and B analogs are disclosed with intermediates and with processes for making them. These compounds differ from the prostaglandins in that they have two fluoro atoms at the C-2 position in place of the two hydrogen atoms at C-2 in the prostaglandins. These compounds are useful for a variety of pharmacological purposes, including anti-ulcer, inhibition of platelet aggregation, increase in nasal patency, labor induction at term, and wound healing.

6 Claims, No Drawings

2,2-DIFLUORO-PGE$_2$ ANALOGS

The present application is a divisional application of Ser. No. 552,708, filed Feb. 24, 1975, now issued as U.S. Pat. No. 4,001,300, on Jan. 4, 1977.

The present invention relates to prostaglandin analogs for which the essential material constituting a disclosure therefor is incorporated by reference here from U.S. Pat. No. 4,001,300, issued Jan. 4, 1977.

I claim:

1. A compound of the formula

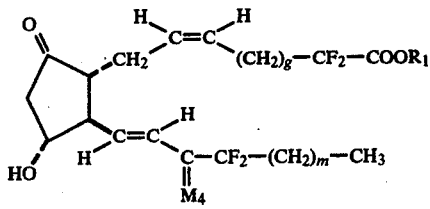

or a mixture comprising that compound and the enantiomer thereof,
wherein g is 2 to 4, inclusive;
wherein M$_4$ is

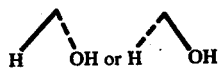

wherein m is 2 to 4, inclusive,
wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro, alkyl of one to 4 carbon atoms, inclusive, or a pharmacologically acceptable cation,

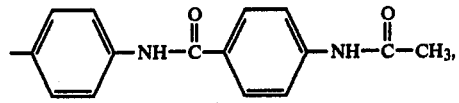

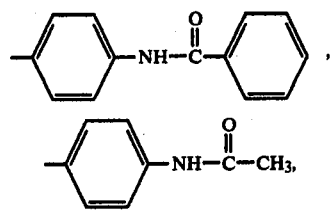

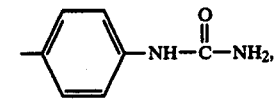

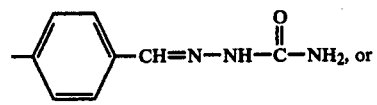

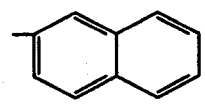

2. A compound according to claim 1, wherein M$_4$ is

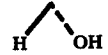

3. A compound according to claim 2, wherein g is 2.
4. A compound according to claim 3, wherein m is 3.
5. 2,2,16,16-Tetrafluoro-PGE$_2$, a compound according to claim 4, wherein R$_1$ is hydrogen.
6. 2,2,16,16-Tetrafluoro-PGE$_2$, methyl ester, a compound according to claim 4, wherein R$_1$ is methyl.

* * * * *